US005674683A

United States Patent [19]
Kool

[11] Patent Number: 5,674,683
[45] Date of Patent: Oct. 7, 1997

[54] STEM-LOOP AND CIRCULAR OLIGONUCLEOTIDES AND METHOD OF USING

[75] Inventor: Eric T. Kool, Rochester, N.Y.

[73] Assignee: Research Corporation Technologies, Inc., Tucson, Ariz.

[21] Appl. No.: 408,656

[22] Filed: Mar. 21, 1995

[51] Int. Cl.$^6$ .......................... C12Q 1/68; C07H 21/00; C07H 21/02; C07H 21/04
[52] U.S. Cl. .......................... 435/6; 536/23.1; 536/24.3; 536/24.31; 536/24.32; 536/24.33
[58] Field of Search .......................... 435/6, 40.51, 40.52, 435/91.1, 91.3; 514/44; 536/23.1, 24.1, 24.2, 24.3, 24.5, 24.31, 24.32, 24.33

[56] References Cited

U.S. PATENT DOCUMENTS 5,208,149  5/1993  Inouye et al. .......................... 435/172.3
5,426,180  6/1995  Kool .......................... 536/25.3

FOREIGN PATENT DOCUMENTS 9217484  10/1992  WIPO.
WO92/19732  11/1992  WIPO.

OTHER PUBLICATIONS

Gura "Antisense has Growing Pains" Science 270 (1995) 575–577.
Kool "Molecular Recognition by Circular Oligonucleotides" J. Am. Chem. Soc. 113 (1991), 6265–6266.
Milligan et al. "Current Concepts in Antisense Drug Design" J. Medicinal Chemistry 36 (1993), 1923–1937.
Simons et al. "Biological Regulation by Antisense RNA . . ." Ann. Rev. Genet. 22 (1988), 567–600.
Cload et al (1991) "Polyether tethered oligonucleotide probes," J. Am. Chem. Soc. 113:6324.
Cooney et al (1988) "Site–specific oligonucleotide binding represses transcription of the human c–myc gene in vitro," Science 241:456.

Goodchild et al (1988) "Inhibition of human immunodeficiency virus replication by antisense oligonucleotides," Proc. Natl. Acad. Sci., 85:5507.
Hobbs et al (1994) "Differential regulation of gene expression in vivo by triple helix forming oligonucleotides as detected by a reporter enzyme," Antisense Research and Development 4:1.
Pilch et al (1994) "Ligand induced formation of nucleic acid triple helices," Proc. Natl. Acad. Sci. 91:9332.
Poddevin (1994) "Improved anti–herpes simplex virus type I activity of a phosphodiester antisense oligonucleotide containing a 3'–terminal hairpin–like structure," Antisense Research and Development 4:147.
Whitton (1994) "Antisense treatment of viral infection" in Advances in Virus Research 44:267, Maramorosch et al, eds, Academic Press, San Diego.
Bannwarth et al (1994) "Short Optimally Capped Duplex DNA as Conformationally Restricted Analogue of B–DNA," Helvetica Chimica Acta 77:182.
Beal et al (1991) "Second Structural Motif for Recognition of DNA by Oligonucleotide–Directed Triple–Helix Formation," Science 251:1360.

(List continued on next page.)

Primary Examiner—John L. LeGuyader
Assistant Examiner—Thomas G. Larson
Attorney, Agent, or Firm—Scully, Scott, Murphy & Presser

[57] ABSTRACT

The present invention provides stem-loop and circular oligonucleotides each with at least one Watson-Crick binding (WC) domain and at least one corresponding Hoogsteen binding (H) domain separated from each other by linker domains. Each WC domain has sufficient complementarity to bind to one strand of a defined nucleic acid target by Watson-Crick base pairing in an anti-parallel orientation. Each corresponding H domain is capable of binding to the WC domain by Hoogsteen base pairing in an anti-parallel manner. The present invention also provides methods of making and using these oligonucleotides as well as kits and pharmaceutical compositions containing these oligonucleotides.

28 Claims, 1 Drawing Sheet

OTHER PUBLICATIONS

Clusel et al (1993) "Ex vivo regulation of specific gene expression by nanomolar concentration of double-stranded dumbbell oligonucleotides," *Nucleic Acids Research* 21:3405.

Erie et al (1989) "Melting Behavior of a Covalently Closed, Single-Stranded, Circular DNA," *Biochemistry* 28:268.

Erie et al (1987) "A Dumbbell-Shaped, Double-Hairpin Structure of DNA: A Thermodynamic Investigation," *Biochemistry* 26:7150.

Giovannangeli et al (1991) "Single-Stranded DNA as a Target for Triple-Helix Formation," *J. Am. Chem. Soc.* 113:7775.

Giovannangeli et al (1993) "Oligonucleotide clamps arrest DNA synthesis on a single-stranded DNA target," *Proc. Natl. Acad. Sci. USA* 90:10013.

Oretskaya et al (1994) "Synthesis of Cyclic Oligodeoxyribonucleotides with Non-Nucleotide Insertions," *Bioorg. Khim.* 20:63.

Prakash et al (1992) "Structural Effects in the Recognition of DNA by Circular Oligonucleotides," *J. Am. Chem. Soc.* 114:3523.

Samadashwily et al (1993) "Suicidal nucleotide sequences for DNA polymerization," *EMBO J.* 12:4975.

Wang et al (1994) "Recognition of Single-Stranded Nucleic Acids by Triplex Formation: The Binding of Pyrimidine-Rich Sequences," *J. Am. Chem. Soc.* 116:8857.

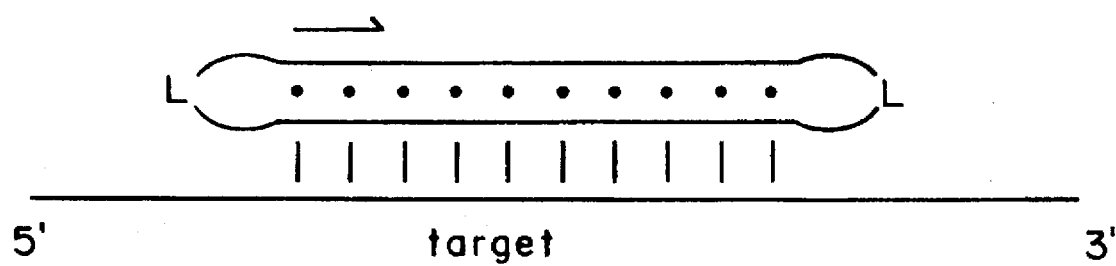
FIG. IA
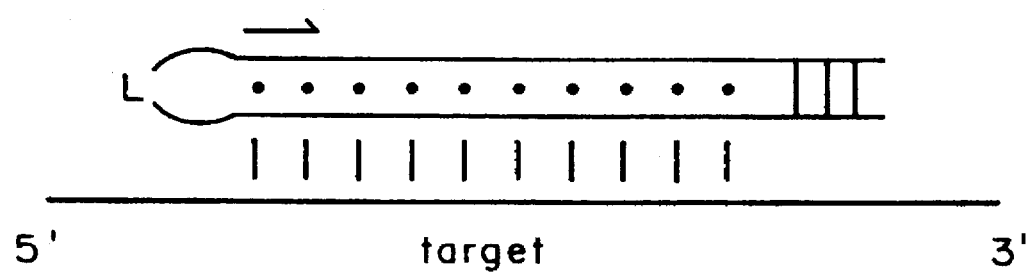
FIG. IB

STEM-LOOP AND CIRCULAR OLIGONUCLEOTIDES AND METHOD OF USING

This invention was made with United States government support under grant GM-46625 awarded by the National Institutes of Health and grant N00014-92-J-1740 awarded by the Office of Naval Research. The United States government has certain rights in the invention.

FIELD OF THE INVENTION

The present invention provides stem-loop and circular oligonucleotides that are capable of binding to nucleic acid targets with high affinity. The oligonucleotides of the present invention are useful in detection and isolation of target nucleic acids, and in inhibiting the biological function of DNA and RNA.

BACKGROUND OF THE INVENTION

An oligonucleotide binds to a target nucleic acid by forming hydrogen bonds between bases in the target and the oligonucleotide. Common B DNA has conventional adenine-thymine (A—T) and guanine-cytosine (G—C) Watson and Crick base pairs with two and three hydrogen bonds, respectively. An understanding of base pairing motifs and duplex and triplex formation has allowed the development of oligonucleotides for a variety of utilities. For example, oligonucleotides can be used as probes for targeting nucleic acids that are immobilized onto a filter or membrane, or are present in tissues. Sambrook et al. (1989, *Molecular Cloning: A Laboratory Manual*, Vols. 1–3, Cold Spring Harbor Press, N.Y.) provide a detailed review of hybridization techniques.

Conventional hybridization technology is based upon the capability of sequence-specific DNA or RNA probes to bind to a target nucleic acid via Watson-Crick hydrogen bonds. Other types of hydrogen bonding patterns are known wherein some atoms of a base that are not involved in Watson-Crick base pairing can form hydrogen bonds to another nucleotide. For example, thymine (T) can bind to an A—T Watson-Crick base pair via hydrogen bonds to the adenine, thereby forming a T—AT base triad. Hoogsteen (1959, *Acta Crystallography* 12:822) first described the alternate hydrogen bonds present in T—AT and C—GC base triads. G—TA base triads, wherein guanine can hydrogen bond with a central thymine, have also been observed (Griffin et al., 1989, *Science* 245:967–971). Beal et al. (1991) *Science* 251:1360 propose models for hydrogen bonding in G—GC, A—AT and T—AT base triplets. Such non-Watson-Crick hydrogen bonding is generally referred to as Hoogsteen bonding.

Oligonucleotides have been observed to bind to duplex DNA by non-Watson-Crick hydrogen bonding in vitro. For example, Cooney et al., 1988, *Science* 241:456 disclose a 27-base single-stranded oligonucleotide which bound to a double-stranded nucleic acid via Hoogsteen base pairing. However, triple-stranded complexes of this type are not very stable, because the oligonucleotide is bound to its target only with less stable alternate hydrogen bonds, i.e., without any Watson-Crick bonds. Further, as disclosed by Beal et al., oligonucleotide directed recognition of double stranded DNA as described by Cooney et al. is limited to binding of purine-rich tracts of DNA.

Giovannangeli et al. (1991, *J. Am. Chem. Soc.* 113:7775 and 1993, *Proc. Natl. Acad. Sci.* 90:10013) disclose oligonucleotides capable of binding to single stranded homopurine DNA targets. The oligonucleotides contain one domain capable of binding to the target by Watson-Crick binding, and a second domain capable of binding to the target strand by parallel Hoogsteen binding. A significant limitation of these oligonucleotides is the requirement for homopurine targets. In addition, linear oligonucleotides are nuclease sensitive, thus limiting their use for many biological applications.

Kool (1991, *J. Am. Chem. Soc.* 113:7775) and Prakash et al. (1992, *J. Am. Chem. Soc.* 114:3523) report circular oligonucleotides capable of binding to single stranded nucleic acids by complexing the target strand on both sides to form a pyrimidine/purine/pyrimidine (pyr/pur/pyr) triplex. In particular, one side of the circular compound is complementary to the target in the antiparallel Watson-Crick sense, whereas the other side of the circle is complementary to the target in the parallel Hoogsteen sense. The use of the circular oligonucleotides is limited to the recognition of purine sequences in the target nucleic acid.

Samadashwily et al. (1993, *EMBO Journal* 12:4975) report that purine-rich linear oligonucleotides, when annealed to a single-stranded template, resulted in termination of polymerization by DNA polymerase in vitro. The linear oligonucleotides were characterized as having triplex forming potential when annealed to a DNA template, but neither actual triplex formation nor binding affinities nor binding to RNA templates were investigated.

In vitro use of oligonucleotides by hybridization technology thus suffers from problems including suboptimal binding affinity. Hybridization technology based upon triplex formation suffers from limitations to particular target sequences such as purines. The development of oligonucleotides for in vivo regulation of biological processes has been hampered by still further problems, including the nuclease sensitivity of linear oligonucleotides.

For example, transcription of the human c-myc gene has been inhibited in a cell free, in vitro assay system by a 27-base linear oligonucleotide designed to bind to the c-myc promoter. Inhibition was only observed using a carefully controlled in vitro assay system wherein lower than physiological temperatures were employed, and many cellular enzymes had been removed or inactivated. These conditions were necessary because linear oligonucleotides bind with low affinity and are highly susceptible to enzymes which degrade linear pieces of DNA (Cooney et al.). Splicing of a pre-mRNA transcript essential for Herpes Simplex virus replication has also been inhibited with a linear oligonucleotide that was complementary to an acceptor splice junction. In this instance, a methylphosphonate linkage was employed in the linear oligonucleotide to increase its nuclease resistance. Addition of this chemically-modified oligonucleotide to the growth medium caused reduction in protein synthesis and growth of uninfected cells, most likely because of toxicity problems at high concentrations (Smith et al., 1986, *Proc. Natl. Acad. Sci. USA* 83:2787–2791).

Linear oligonucleotides have been examined for the ability to inhibit human immunodeficiency virus replication in cultured cells (Goodchild et al., 1988, *Proc. Natl. Acad. Sci. USA* 85:5507–5511). Linear oligonucleotides complementary to sites within or near the terminal repeats of the retrovirus genome and within sites complementary to certain splice junctions were most effective in blocking viral replication. However, these experiments required large amounts of the linear oligonucleotides before an effect was obtained, presumably because of the low binding stability and vulnerability of these linear oligonucleotides to nucleases.

Accordingly, there is a need in the art for stable oligonucleotide compounds capable of strong and specific binding to nucleic acids, and in particular to pyrimidine rich nucleic acids. The present invention represents an innovation characterized by a substantial improvement relative to the prior art since the subject stem-loop and circular oligonucleotides exhibit high specificity, low or no toxicity, and more resistance to nucleases than linear oligonucleotides, while binding to single-stranded pyrimidine rich target nucleic acids more strongly than conventional linear oligonucleotides.

SUMMARY OF THE INVENTION

The present invention provides circular oligonucleotides having at least one first binding domain capable of detectably binding to a defined nucleic acid target by antiparallel Watson-Crick base pairing (hereinafter the WC domain), and at least one second binding domain capable of binding to the first binding domain by antiparallel Hoogsteen base pairing (hereinafter the H domain). The circular nucleotides of the invention further comprise a linker domain separating each binding domain.

The present invention is further directed to stem-loop oligonucleotides comprising a double-stranded stem domain of at least about two base pairs and a loop domain having at least one first binding domain capable of binding to a defined nucleic acid target by antiparallel Watson-Crick base pairing, and at least one second binding domain capable of binding to the first binding domain by antiparallel Hoogsteen base pairing. The binding domains are separated by a linker domain.

In the case where multiple binding domains are included in the stem-loop and circular oligonucleotides of the present invention, the linker domains separating the binding domains can constitute, in whole or in part, another binding domain that functions as a binding domain in an alternate conformation. In other words, depending upon the particular target, a binding domain can also function as a linker domain for another binding domain and vice versa.

Another aspect of the present invention provides the subject stem-loop and circular oligonucleotides derivatized with a reporter group to provide a probe for a target nucleic acid, or with a drug or other pharmaceutical agent to provide cell specific drug delivery, or with agents which can cleave or otherwise modify the target nucleic acid or, furthermore, with agents that can facilitate cellular uptake or target binding of the oligonucleotide.

An additional aspect of the present invention provides stem-loop or circular oligonucleotides linked to a solid support for isolation of a nucleic acid complementary to the oligonucleotide.

Another aspect of the present invention provides a compartmentalized kit for detection, diagnosis or isolation of a target nucleic acid including at least one first container providing at least one of the present stem-loop or circular oligonucleotides.

A further aspect of the present invention provides a method of detecting a target nucleic acid which involves contacting a stem-loop or circular oligonucleotide of the present invention with a sample containing the target nucleic acid, for a time and under conditions sufficient to form an oligonucleotide-target complex, and detecting the complex.

A still further aspect of the present invention provides a method of regulating biosynthesis of a DNA, an RNA or a protein. This method includes contacting at least one of the subject stem-loop or circular oligonucleotides with a nucleic acid template for the DNA, the RNA or the protein under conditions sufficient to permit binding of the oligonucleotide to a target sequence contained in the template.

The present invention further provides a method of cell specific drug delivery comprising administering to a mammal a drug covalently linked to a stem-loop or circular oligonucleotide of the present invention.

An additional aspect of the present invention provides pharmaceutical compositions for regulating biosynthesis of a nucleic acid or protein containing a biosynthesis regulating amount of at least one of the subject oligonucleotides and a pharmaceutically acceptable carrier.

BRIEF DESCRIPTION OF THE DRAWINGS

FIGS. 1A and 1B present schematic illustrations of the relative orientations of representative circular and stem-loop oligonucleotides, respectively. Arrows indicate 5' to 3' directionality, linker domains are indicated by L, Watson Crick base pairs are indicated by lines and Hoogsteen base pairs are indicated by dots. Stem-loop oligonucleotides may also be in the opposite orientation, i.e. the stem may be at the 5' or 3' end.

DETAILED DESCRIPTION OF THE INVENTION

The present invention relates to stem-loop and circular oligonucleotides that can bind to nucleic acid targets with higher affinity, selectivity and stability than a corresponding linear oligonucleotide.

Furthermore, the nuclease resistance and the strong, selective binding of the subject stem-loop and circular oligonucleotides to nucleic acid targets provides a variety of uses, including methods of regulating such biological processes as DNA replication, RNA transcription, RNA splicing and processing, protein translation and the like. Additionally, the present oligonucleotides are useful for isolation of complementary nucleic acids or for sequence-specific delivery of drugs or other molecules into cells.

The circular oligonucleotides of the present invention have at least one first binding domain capable of detectably binding to a defined nucleic acid target by antiparallel Watson-Crick base pairing (the WC domain), and at least one second binding domain capable of binding to the first binding domain by antiparallel Hoogsteen base pairing (the H domain). The circular nucleotides of the invention further comprise a linker domain separating each binding domain. In a preferred embodiment, the circular oligonucleotide has one WC domain and one corresponding H domain separated by linker domains of two or three oligonucleotides.

The stem-loop oligonucleotides of the present invention comprise a double-stranded stem domain of at least about two base pairs and a loop domain having at least one first binding domain capable of binding to a defined nucleic acid target by antiparallel Watson-Crick base pairing (the WC domain), and at least one second binding domain capable of binding to the first binding domain by antiparallel Hoogsteen base pairing (the H domain). The binding domains are separated by a linker domain. In a preferred embodiment, the stem-loop oligonucleotide has one WC domain and one corresponding H domain separated by linker domains of two or three nucleotides.

As defined herein, antiparallel binding means that the 5' to 3' orientations of two strands are in opposite directions, i.e. the strands are aligned as found in the typical Watson-Crick base pairing arrangement of double helical DNA. Schematic illustrations of the relative orientations of representative circular and stem-loop oligonucleotides are set forth in FIGS. 1A and 1B, respectively. Arrows indicate 5' to 3' directionality, linker domains are indicated by L, Watson Crick base pairs are indicated by lines and Hoogsteen base pairs are indicated by dots. The stem of the stem-loop oligonucleotides may be at the 5' or 3' end.

When more than one WC and H binding domains are present, such binding domains are separated from other binding domains by linker domains of sufficient length to permit binding to multiple targets. Moreover, when a stem-loop or circular oligonucleotide has multiple WC and H domains, a linker domain for one pair of corresponding WC and H binding domains can constitute a WC or H domain for binding to another target. When an oligonucleotide of the present invention includes, e.g., two pairs of corresponding binding domains, these pairs of corresponding binding domains can also bind separate target sites. Moreover, when an oligonucleotide has multiple WC and H domains, the corresponding targets need not be present on one nucleic acid strand. Furthermore, a linker domain of a stem-loop or circular oligonucleotide bound to a given target can be a WC or H domain for binding to a second target when the oligonucleotide is released from the first target.

The nucleotide sequences of the WC and H domains of the subject stem-loop and circular oligonucleotides are determined with reference to a defined nucleic acid target. The base pairing rules provided hereinbelow define what is referred to herein as Watson Crick and Hoogsteen base pairing.

The defined nucleic acid target may be DNA or RNA and is preferably single-stranded. Double-stranded targets are also contemplated, and in a preferred embodiment a double-stranded target is subjected to denaturating conditions, ionic strength conditions or other conditions that provide strand opening or strand displacement such that a single strand is available for binding to the oligonucleotide of the present invention.

A target may be selected by its known functional and structural characteristics. For example, some preferred targets can be coding regions, origins of replication, reverse transcriptase binding sites, transcription regulatory elements, RNA splicing junctions, or ribosome binding sites, among others. Messenger RNA and viral DNA and RNA are particularly preferred targets. A target can also be selected to effect the detection or isolation of a DNA or RNA template. Double-stranded DNA and RNA that have been subjected to denaturation are preferred targets for in vitro and in situ applications. Preferred targets are rich in pyrimidines, i.e. in cytosine, uracil and thymine.

The nucleotide sequence of the target DNA or RNA may be known in full or in part. When the target nucleotide sequence is completely known, the sequence of the WC domain is designed with the necessary degree of complementarity to achieve binding, as detected by known procedures, for example by a change in light absorption or fluorescence. In some instances, the target sequence may be represented by a consensus sequence or may be only partially known. In this instance a target may match the consensus sequence exactly or may have some mismatched bases, but not enough mismatch to prevent binding. Likewise, if a portion of a target sequence is known, one skilled in the art can refer to the base pairing rules provided hereinbelow to design oligonucleotides that detectably bind to the target with higher affinity than a corresponding linear oligonucleotide.

The sequence of the WC domain of the subject stem-loop and circular oligonucleotides is determined by the following base pairing rules with reference to a defined nucleic acid target.

The general rules for determining the sequence of a sufficient number of nucleotides of the WC domain are as follows: when a base for a position in the target is guanine, or a guanine analog, then WC has cytosine or uracil or pseudouracil, or suitable analogs thereof, in a corresponding position;

when a base for a position in the target is adenine, or an adenine analog, then WC has thymine or uracil or pseudouracil, or suitable analogs thereof, in a corresponding position;

when a base for a position in the target is thymine, or a thymine analog, then WC has adenine, or a suitable analog thereof, in a corresponding position; and when a base for a position in the target is cytosine, or a cytosine analog, then WC has a guanine, or a suitable analog thereof, in corresponding position;

when a base for a position in the target is uracil, or a uracil analog, then WC has adenine or guanine, or suitable analogs thereof, in a corresponding position.

In particular, a sufficient number of nucleotide positions of the WC domain is determined according to the foregoing rules such that detectable binding is achieved. Detectable binding is defined herein as binding of the oligonucleotide to the target such that the formation of a resulting complex can be detected by methods well-known in the art, including for example the determination of a change in light absorption upon binding or melting. Accordingly, the base pairing rules must be satisfied to the extent needed to achieve detectable binding of a stem-loop or circular oligonucleotide to its nucleic acid target. The degree of complementarity, i.e. adherence to the base-pairing rules, need not be 100% so long as binding can be detected. For the present invention sufficient complementarity means that a sufficient number of base pairs exist between a target nucleic acid and the WC domain of the circular or stem-loop oligonucleotide to achieve detectable binding. When expressed or measured by percentage of base pairs formed, the degree of complementarity can range from as little as about 30–40% complementarity to full, i.e. 100%, complementarity. In general, the overall degree of complementarity between the WC domain and the target is preferably at least about 50%, and more preferably about 90%. In a most preferred embodiment, the degree of complementarity between the target and the WC domain is 100%.

Moreover, the degree of complementarity that provides detectable binding between the subject circular oligonucleotides and the respective targets is dependent upon the conditions under which that binding occurs. It is well known that binding, i.e. hybridization, between nucleic acid strands depends on factors besides the degree of mismatch between two sequences. Such factors include the GC content of the region, temperature, ionic strength, the presence of formamide and types of counter ions present. The effect of these conditions upon binding is known to one skilled in the art. Furthermore, conditions are frequently determined by the circumstances of use. For example, when a circular oligonucleotide is made for use in vivo, no formamide will be present and the ionic strength, types of counter ions, and temperature correspond to physiological conditions. Binding conditions can be manipulated in vitro to optimize the utility of the present oligonucleotides. A thorough treatment of the qualitative and quantitative considerations involved in establishing binding conditions that allow one skilled in the art to design appropriate oligonucleotides for use under the desired conditions is provided by Beltz et al., 1983, *Methods Enzymol.* 100:266–285 and by Sambrook et al.

As used herein "binding" or "stable binding" means that a sufficient amount of the oligonucleotide is bound or hybridized to its target to permit detection of that binding. Binding can be detected by either physical or functional properties of the target:circular oligonucleotide complex. Binding between a target and an oligonucleotide can be detected by any procedure known to one skilled in the art, including both functional or physical binding assays. Binding may be detected functionally by determining whether binding has an observable effect upon a biosynthetic process such as DNA replication, RNA transcription, protein translation and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, a method that is widely used, because it is simple and reliable, involves observing a change in light absorption of a solution containing an oligonucleotide and a target nucleic acid at 220 to 300 nm as the temperature is slowly increased. If the oligonucleotide has bound to its target, there is a sudden increase in absorption at a characteristic temperature as the oligonucleotide and target dissociate or melt.

Having determined the sequence of the WC domain with reference to a defined nucleic acid target and the base pairing rules described hereinabove, the sequence of the H domain is determined with reference to the corresponding WC domain. The sequence of the H domain is determined such that the H domain binds in antiparallel manner to the corresponding WC domain by Hoogsteen base pairing. Antiparallel Hoogsteen base pairing is also referred to herein as reverse Hoogsteen binding. Hoogsteen binding or base pairing is defined herein as binding in accordance with the following base pairing rules. These general rules are used for determining the sequence of the H domain:

- when a base for a position in the WC domain is guanine or a guanine analog, then H has guanine or a suitable analog thereof, in a corresponding position;
- when a base for a position in the WC domain is adenine or an adenine analog, then H has adenine or thymine or uracil, or suitable analogs thereof, in a corresponding position;
- when a base for a position in the WC domain is thymine, cytosine, uracil, or analogs thereof, then H has adenine, cytosine, guanine, thymine, uracil, imidazole, or suitable analogs thereof, in a corresponding position.

The presence of the H domain in the subject stem-loop and circular oligonucleotides serves to increase the binding affinity of the present oligonucleotides relative to corresponding linear oligonucleotides. While not being limited to a particular mechanism, the subject oligonucleotides presumably bind directly to the target only by the WC domain, and the Hoogsteen interactions between the H and WC domain serve to rigidify the oligonucleotide and provide a benefit in complexation. Accordingly, the binding affinity of the present oligonucleotides is optimal when 100% of the nucleotides in the H domain are determined by the above base pairing rules relative to the WC domain. However, a certain amount of mismatch in the H domain can be tolerated with retention of a gain in binding affinity relative to Watson-Crick binding alone. The ordinarily skilled artisan can determine the tolerable amount of mismatch under given conditions. In accordance with the present invention, the sequence of the H domain must be determined in accordance with the above base pairing rules only to the degree that the resulting oligonucleotide exhibits an increased binding affinity for a particular target relative to a corresponding linear oligonucleotide. A corresponding linear oligonucleotide is one that contains only the sequence of the WC domain, i.e. is complementary to the target in a Watson-Crick sense. In a preferred embodiment, 50–100% of the nucleotides in the H domain are determined in accordance with the base pairing rules. In a more preferred embodiment, 80–100% of the nucleotides in the H domain are determined in accordance with the base pairing rules. In a most preferred embodiment, 100% of the nucleotides in the H domain are determined in accordance with the base pairing rules.

In a preferred embodiment of the present invention, the nucleic acid target is pyrimidine rich; RNA targets are UC rich, and DNA targets are TC rich. In accordance with the above base pairing rules, the WC domains of the subject stem-loop and circular oligonucleotides are thus AG rich and the H domains are thus TG rich. In a preferred embodiment, the potential triplexes formed by binding of nucleotides from the H/WC/target domains are GGC, GGU, AAT, TAT, UAT, AAU, UAU and TAU.

Each WC and H domain can independently have about 2 to about 200 nucleotides with preferred lengths being about 6 to about 80 nucleotides. The most preferred lengths are 8 to 36 nucleotides.

The double stranded stems of the stem-loop oligonucleotides of the present invention are formed by base pairing of complementary bases in the 5' and 3' ends of the oligonucleotide and are at least about two base pairs in length. A preferred length is from about three base pairs to about ten base pairs. The stem is preferably kept as short as possible without adversely affecting the stability of the stem-loop structure, although longer stems are also contemplated. Short stems are less likely to cause steric hindrance of binding of oligonucleotide to target. The stem may further comprise an overhanging single-stranded region, i.e. the strand may be a partial duplex. The two strands of the stem can be covalently cross-linked such that the stability of the stem structure is independent of its length. Thus the stem length need only be long enough to permit cross linking, i.e. about two base pairs. Cross-linking may be performed by procedures known to one of ordinary skill in the art, e.g. as described by Calabresi et al. in Gilman et al., eds. *The Pharmacological Basis of Therapeutics*, 1980, MacMillan Publishing Co., Inc., pp. 1256–1272 and Glick et al. (1992) *J. Am. Chem. Soc.* 114:5447. Further, a nucleotide linker as described herein may be used to covalently link the base of the stem.

The stem-loop and circular oligonucleotides are DNA or RNA, or hybrids of DNA and RNA. For example, the subject oligonucleotides can comprise: a DNA binding domain and an RNA binding domain; RNA binding domains and DNA linkers; all RNA; all DNA; RNA interspersed with 2'-O-methyl RNA, and so on. The oligonucleotides comprise the bases guanine (G), adenine (A), thymine (T), cytosine (C) or uracil (U) in the nucleotides, or any nucleotide analog that is capable of hydrogen bonding in an anti-parallel manner. Nucleotide analogs include pseudocytidine, isopseudocytidine, imidazole, 3-aminophenyl-imidazole, 2'-O-methyladenosine, 7-deazadenosine, 7-deazaguanosine, 7-deazaxanthosine, 4-acetylcytidine, 5-(carboxyhydroxylmethyl)-uridine, 2'-O-methylcytidine, 5-carboxymethylaminomethyl-2-thioridine, 5-carboxymethylamino-methyluridine, dihydrouridine, 2'-O-methyluridine, pseudouridine, 2'-O-methyl-pseudouridine, beta,D-galactosylqueosine, 2'-O-methylguanosine, inosine, N6-isopentenyladenosine, 1-methyladenosine, 1-methyl-pseudouridine, 1-methylguanosine, 1-methylinosine, 2,2-dimethylguanosine, 2-methyladenosine, 2-methylguanosine, 3-methylcytidine, 5-methylcytidine, 5-methyluridine, N6-methyl-adenosine, 7-methylguanosine, 5-methylamino-methyluridine, 5-methoxyaminomethyl-2-thiouridine, β-D-mannosylqueosine, 5-methoxycarbonylmethyluridine, 5-methoxyuridine, 2-methyl-thio-N6-isopentenyladenosine, N-(9-beta-D-ribofuranosyl-2-methylthiopurine-6-yl)carbamoyl)threonine, N-(9-beta-D-ribofuranosylpurine-6-yl)-N-methylcarbamoyl)threonine and thioguanosine. Either ribose or deoxyribose sugars can be used with these analogs. Modified sugars, such as 2'-O-methyl ribose, are also contemplated. Nucleotides bases in an α-anomeric conformation can also be used in the stem-loop and circular oligonucleotides of the present invention.

Preferred nucleotide analogs are unmodified G, A, T, C and U nucleotides; pyrimidine analogs with lower alkyl, alkynyl or alkenyl groups in the 5 position of the base and purine analogs with similar groups in the 7 or 8 position of the base. Especially preferred nucleotide analogs are 5-methylcytosine, 5-methyluracil, diaminopurine, and nucleotides with a 2'-O-methylribose moiety in place of ribose or deoxyribose. As used herein lower alkyl, lower alkynyl and lower alkenyl contain from 1 to 6 carbon atoms and can be straight chain or branched. These groups include methyl, ethyl, propyl, isopropyl, butyl, isobutyl, tertiary butyl, amyl, hexyl and the like. A preferred alkyl group is methyl.

The WC and H domains are separated by linker domains which can independently have from about 1 to about 2000 nucleotides. A preferred linker length is from about 1 to about 10 nucleotides with an especially preferred length being about 2 or 3 nucleotides. In a preferred embodiment, the linker is C—C or T—T. The stem domain is considered to contribute two nucleotides to the linker domain separating the WC and H domains of the subject stem-loop oligonucleotides.

According to the present invention, the linker domains may be non-nucleotide linkers. Non-nucleotide linkers can make the present stem-loop and circular oligonucleotides less expensive to produce. More significantly, oligonucleotides with non-nucleotide loops are more resistant to nucleases (Rumney and Kool, 1992, Angewandte Chemie, Intl. Ed., 31:1617) and therefore have a longer biological half-life than linear oligonucleotides. Furthermore, linkers having no charge, or a positive charge, can be used to promote binding by eliminating negative charge repulsions between the linker and target. In addition, oligonucleotides having uncharged or hydrophobic non-nucleotide linkers can penetrate cellular membranes better than oligonucleotides with nucleotide loops.

As contemplated herein, non-nucleotide linker domains can be composed of alkyl chains, polyethylene glycol or oligoethylene glycol chains or other chains providing the necessary steric or flexibility properties which are compatible with oligonucleotide synthesis. The length of these chains is equivalent to about 2 to about 2000 nucleotides, with preferred lengths equivalent to about 2 to about 8 nucleotides. The most preferred length for these chains is equivalent to about 2 to 4 nucleotides.

Preferred chains for non-nucleotide linker domains are polyethylene glycol or oligoethylene glycol chains. In particular, oligoethylene glycol chains having a length similar to a 2 to 4 nucleotide chain, e.g. a di-, tri-, tetra-, penta- or hexaethylene glycol chain, are preferred but longer oligoethylene glycol chains are contemplated. Covalent bonds such as disulfide bonds can also function as linker domains.

The circular oligonucleotides of the present invention can be made first as linear oligonucleotides and then circularized. Linear oligonucleotides can be made by any of a myriad of procedures known for making DNA or RNA oligonucleotides. For example, such procedures include enzymatic synthesis and chemical synthesis.

Enzymatic methods of DNA oligonucleotide synthesis frequently employ Klenow, T7, T4, Taq or E. coli DNA polymerases as described in Sambrook et al. Enzymatic methods of RNA oligonucleotide synthesis frequently employ SP6, T3 or T7 RNA polymerase as described in Sambrook et al. Reverse transcriptase can also be used to synthesize DNA from RNA (Sambrook et al.). To prepare oligonucleotides enzymatically requires a template nucleic acid which can either be synthesized chemically, or be obtained as mRNA, genomic DNA, cloned genomic DNA, cloned cDNA or other recombinant DNA. Some enzymatic methods of DNA oligonucleotide synthesis can require an additional primer oligonucleotide which can be synthesized chemically. Finally, linear oligonucleotides can be prepared by polymerase chain reaction (PCR) techniques as described, for example, by Saiki et al., 1988, Science 239:487.

Chemical synthesis of linear oligonucleotides is well known in the art and can be achieved by solution or solid phase techniques. Moreover, linear oligonucleotides of defined sequence can be purchased commercially or can be made by any of several different synthetic procedures including the phosphoramidite, phosphite triester, H-phosphonate and phosphotriester methods, typically by automated synthesis methods. The synthesis method selected can depend on the length of the desired oligonucleotide and such choice is within the skill of the ordinary artisan. For example, the phosphoramidite and phosphite triester method produce oligonucleotides having 175 or more nucleotides while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann et al. (1990, Chemical Reviews 90:543–584) provide references and outline procedures for making oligonucleotides with modified bases and modified phosphodiester linkages.

Synthetic linear oligonucleotides may be purified by polyacrylamide gel electrophoresis, or by any of a number of chromatographic methods, including gel chromatography and high pressure liquid chromatography. To confirm a nucleotide sequence, oligonucleotides may be subjected to DNA sequencing by any of the known procedures, including Maxam and Gilbert sequencing, Sanger sequencing, capillary electrophoresis sequencing, the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, J. Am. Chem. Soc. 104:976; Viari, et al., 1987, Biomed. Environ. Mass Spectrom. 14:83; Grotjahn et al., 1982, Nuc. Acid Res. 10:4671). Sequencing methods are also available for RNA oligonucleotides.

The present invention provides several methods of preparing circular oligonucleotides from linear precursors (i.e.

precircles), including a method wherein a precircle is synthesized and bound to an end-joining-oligonucleotide and the two ends of the precircle are joined. Any method of joining two ends of an oligonucleotide is contemplated by the present invention, including chemical methods employing, for example, known coupling agents like BrCN, N-cyanoimidazole ZnCl$_2$, 1-ethyl-3-(3-dimethylaminopropyl)carbodiimide and other carbodiimides and carbonyl diimidazoles. Furthermore, the ends of a precircle can be joined by condensing a 5' phosphate and a 3' hydroxy, or a 5' hydroxy and a 3' phosphate.

A simple one-step chemical method to construct the subject circular oligonucleotides from precircles is provided in U.S. application Ser. No. 08/044,800. An oligonucleotide is constructed which has the same sequence as the target nucleic acid; this is the end-joining oligonucleotide. A DNA or RNA linear precircle is chemically or enzymatically synthesized and phosphorylated on its 5' or 3' end, again by either chemical or enzymatic means. The precircle and the end-joining oligonucleotide are mixed and annealed, thereby forming a complex in which the 5' and 3' ends of the precircle are adjacent. It is preferred that the ends of the precircle fall within a binding domain, not within a linker. Moreover, it is preferred that a precircle have a 3'-phosphate rather than a 5'-phosphate. After complex formation, the ends undergo a condensation reaction in a buffered aqueous solution containing divalent metal ions and BrCN at about pH 7.0. In a preferred embodiment the buffer is imidazole-Cl at pH 7.0 with a divalent metal such as Ni, Zn, Mn, or Co. Ni is the most preferred divalent metal. Condensation occurs after about 6–48 hr. of incubation at 4°–37° C. Other divalent metals, such as Cu, Pb, Ca and Mg, can also be used.

One method for RNA circularization incorporates the appropriate nucleotide sequences, preferably in a linker domain, into an RNA oligonucleotide to promote self splicing, since a circular product is formed under the appropriate conditions (Sugimoto et al., 1988, *Biochemistry* 27:6384–6392).

Enzymatic circle closure is also possible using DNA ligase or RNA ligase under conditions appropriate for these enzymes.

Circular oligonucleotides can be separated from the end joining oligonucleotide by denaturing gel electrophoresis or melting followed by gel electrophoresis, size selective chromatography, or other appropriate chromatographic or electrophoretic methods. The recovered circular oligonucleotide can be further purified by standard techniques as needed for its use in the methods of the present invention. Alternately, the end joining oligonucleotide may be attached to a solid support and recovered by filtration.

The subject stem-loop oligonucleotides can be made by the procedures described hereinabove for the synthesis of linear oligonucleotides. The present stem-loop oligonucleotides can be also made recombinantly by placing a nucleic acid having a sequence which is complementary to the desired stem-loop oligonucleotide into an expression vector. Such an expression vector minimally encodes a segment which can effect expression of the stem-loop oligonucleotide when the segment is operably linked to the nucleic acid encoding the stem-loop oligonucleotide. However, such an expression vector can also encode additional elements such as origins of replication, selectable markers, transcription termination signals, centromeres, autonomous replication sequences.

As used herein, an expression vector can be a replicable or a non-replicable expression vector. Further, the expression vectors of the present invention can be chromosomally integrating or chromosomally nonintegrating expression vectors, and may be designed to function in prokaryotic, yeast, insect or mammalian cells.

The present invention also contemplates derivatization or chemical modification of the subject oligonucleotides with chemical groups to facilitate cellular uptake. For example, covalent linkage of a cholesterol moiety to an oligonucleotide can improve cellular uptake by 5- to 10-fold which in turn improves DNA binding by about 10-fold (Boutorin et al., 1989, *FEBS Letters* 254:129–132). Other ligands for cellular receptors may also have utility for improving cellular uptake, including, e.g. insulin, transferrin and others. Similarly, derivatization of oligonucleotides with poly-L-lysine can aid oligonucleotide uptake by cells (Schell, 1974, *Biochem. Biophys. Acta* 340:323, and Lemaitre et al., 1987, *Proc. Natl. Acad., Sci. USA* 84:648). Certain protein carriers can also facilitate cellular uptake of oligonucleotides, including, for example, serum albumin, nuclear proteins possessing signals for transport to the nucleus, and viral or bacterial proteins capable of cell membrane penetration. Therefore, protein carriers are useful when associated with or linked to the circular oligonucleotides of this invention. Accordingly, the present invention contemplates derivatization of the subject stem-loop and circular oligonucleotides with groups capable of facilitating cellular uptake, including hydrocarbons and non-polar groups, cholesterol, poly-L-lysine and proteins, as well as other aryl or steroid groups and polycations having analogous beneficial effects, such as phenyl or naphthyl groups, quinoline, anthracene or phenanthracene groups, fatty acids, fatty alcohols and sesquiterpenes, diterpenes and steroids.

The present invention further contemplates derivatization of the subject oligonucleotides with agents that can cleave or modify the target nucleic acid or other nucleic acid strands associated with or in the vicinity of the target. For example, viral DNA or RNA can be targeted for destruction without harming cellular nucleic acids by administering a stem-loop or circular oligonucleotide having a WC domain that is complementary to the targeted nucleic acid which is linked to an agent that, upon binding, can cut or render the viral DNA or RNA inactive. Nucleic acid destroying agents that are contemplated by the present invention as having cleavage or modifying activities include, for example, RNA and DNA nucleases, ribozymes that can cleave RNA, azidoproflavine, acridine, EDTA/Fe, chloroethylamine, azidophenacyl and phenanthroline/Cu. Uhlmann et al. (1990, *Chemical Reviews* 90:543–584) provide further information on the use of such agents and methods of derivatizing oligonucleotides that can be adapted for use with the subject oligonucleotides.

Derivatization of the subject stem-loop and circular oligonucleotides with groups that facilitate cellular uptake or target binding, as well as derivatization with nucleic acid destroying agents or drugs, can be done by any of the procedures known to one skilled in the art. Moreover, the desired groups can be added to nucleotides before synthesis of the oligonucleotide. For example, these groups can be linked to the 5-position of T or C and these modified T and C nucleotides can be used for synthesis of the present oligonucleotides. In addition, derivatization of selected nucleotides permits incorporation of the group into selected domains of the subject oligonucleotides. For example, in some instances it is preferable to incorporate certain groups into a linker where that group will not interfere with binding, or into a WC domain to facilitate cleavage or modification of the target nucleic acid.

In accordance with the present invention, modification in the phosphodiester backbone of the subject oligonucleotides is also contemplated. Such modifications can aid uptake of the oligonucleotide by cells or can extend the biological half-life of such nucleotides. For example, the subject oligonucleotides may penetrate the cell membrane more readily if the negative charge on the internucleotide phosphate is eliminated. This can be done by replacing the negatively charged phosphate oxygen with a methyl group, an amine or by changing the phosphodiester linkage into a phosphotriester linkage by addition of an alkyl group to the negatively charged phosphate oxygen. Alternatively, one or more of the phosphate atoms that are part of the normal phosphodiester linkage can be replaced. For example, NH—P, $CH_2$—P or S—P linkages can be formed. Accordingly, the present invention contemplates using methylphosphonates, phosphorothioates, phosphorodithioates, phosphotriesters and phosphorusboron (Sood et al., 1990, *J. Am. Chem. Soc.* 112:9000) linkages. The phosphodiester group can be replaced with siloxane, carbonate, acetamidate or thioether groups. These modifications can also increase the resistance of the subject oligonucleotides to nucleases. Methods for synthesis of oligonucleotides with modified phosphodiester linkages are reviewed by Uhlmann et al.

Stem-loop and circular oligonucleotides with non-nucleotide linkers can be prepared by any known procedure. For example, Durand et al. (1990, *Nucleic Acids Res.* 18:6353–6359) provide synthetic procedures for linking non-nucleotide chains to DNA. Such procedures can generally be adapted to permit an automated synthesis of a linear oligonucleotide precursor which is then used to make a stem-loop or circular oligonucleotide of the present invention. In general, groups reactive with nucleotides in standard DNA synthesis, e.g. phosphoramidite, H-phosphonate, dimethoxytrityl, monomethoxytrityl and the like, can be placed at the ends of non-nucleotide chains and nucleotides corresponding to the ends of WC and H domains can be linked thereto.

Additionally, different nucleotide sugars can be incorporated into the oligonucleotides of this invention. Additional binding stability can be provided by using 2'-O-methyl ribose in the present oligonucleotides. Phosphoramidite chemistry can be used to synthesize RNA oligonucleotides as described (Reese, C. B. in *Nucleic Acids & Molecular Biology;* Springer-Verlag: Berlin, 1989; Vol. 3, p. 164; and Rao et al., 1987, *Tetrahedron Lett.* 28:4897).

The synthesis of RNA 2'-O-methyloligoribonucleotides and DNA oligonucleotides differ only slightly. RNA 2'-O-methyloligonucleotides can be prepared with minor modifications of the amidite, H-phosphonate or phosphotriester methods (Shibahara et al, 1987, *Nucleic Acids Res.* 15:4403; Shibahara et al., 1989, *Nucleic Acids Res.* 17:239; Anoue et al., 1987, *Nucleic Acids Res.*15:6131).

The present invention contemplates a variety of utilities for the subject stem-loop and circular oligonucleotides which are made possible by their selective and stable binding properties with nucleic acid targets, nuclease resistance, and lack of toxicity. Some utilities include, but are not limited to: use of the subject oligonucleotides of defined sequence, bound to a solid support, for affinity isolation of complementary nucleic acids; use of the subject oligonucleotides to provide sequence specific stop signals during polymerase chain reaction (PCR); covalent attachment of a drug, drug analog or other therapeutic agent to the subject oligonucleotides to allow cell type specific drug delivery; labeling the stem-loop or circular oligonucleotides with a detectable reporter molecule for localizing, quantitating or identifying complementary target nucleic acids; and binding the subject oligonucleotides to a cellular or viral nucleic acid template and regulating biosynthesis directed by that template.

The nucleic acid templates useful in the methods of the present invention can be RNA or DNA and can be single-stranded or double-stranded. In a preferred embodiment the nucleic acid template is single-stranded DNA or RNA. In another preferred embodiment the nucleic acid target is mRNA or viral DNA or RNA. In a most preferred embodiment the nucleic acid target is pryimidine rich, single-stranded DNA or RNA. In accordance with the present invention, pyrimidine rich refers to targets containing at least 50% pyrimidines. In a preferred embodiment the pyrimidine rich targets contain at least 70% pyrimidines. In a most preferred embodiment, the pyrimidine rich targets contain from 90–100% pyrimidines. Double-stranded templates that are opened during biosynthetic processes or that can be denatured are also contemplated as targets.

The skilled artisan can determine the appropriate composition of the subject oligonucleotides by the base pairing rules and further considerations addressed herein for particular diagnostic and therapeutic applications, and with reference to the desired target nucleic acid. It has been discovered in accordance with the present invention that DNA oligonucleotides are useful for targeting both DNA and RNA templates. Further RNA oligonucleotides are useful for targeting both DNA and RNA templates. DNA oligonucleotides are preferred for binding to RNA targets.

In a method of isolation of a target nucleic acid, the subject oligonucleotides can be attached to a solid support such as silica, cellulose, nylon, polyacrylamide, polystyrene, agarose and other natural or synthetic materials that are used to make beads, filters, and column chromatography resins. Attachment procedures for nucleic acids to solid supports of these types are well known; any known attachment procedure is contemplated by the present invention. A stem-loop or circular oligonucleotide attached to a solid support can then be used to isolate a complementary nucleic acid. Isolation of the complementary nucleic acid can be done by incorporating the oligonucleotide:solid support into a column for chromatographic procedures. Other isolation methods can be done without incorporation of the oligonucleotide:solid support into a column, e.g. by utilization of filtration procedures. The subject stem-loop and circular oligonucleotides are ideally suited to applications of this type because they are nuclease resistant and bind target nucleic acids so strongly.

Further utilities are available for the subject oligonucleotides in the field of polymerase chain reaction (PCR) technology. PCR technology provides methods of synthesizing a double-standard DNA fragment encoded in a nucleic acid template between two known nucleic acid sequences which are employed as primer binding sites. The subject oligonucleotides can be used to selectively prevent amplification of a particular species, e.g. a mutant or allelic variant of known sequence. This can be done by, for example, binding a circular oligonucleotide of the present invention to one of the primer binding sites or to a site lying between the primer binding sites.

The present invention also contemplates using the subject oligonucleotides for targeting drugs to specific cell types. Such targeting can allow selective destruction or enhancement of particular cell types, e.g. inhibition of tumor cell growth can be attained. Different cell types express different genes, so that the concentration of a particular mRNA can be greater in one cell type relative to another cell type. Such an mRNA is a target mRNA for cell type specific drug delivery by stem-loop or circular oligonucleotides linked to drugs or drug analogs. Cells with high concentrations of target mRNA are targeted for drug delivery by administering to the cell an drug-conjugated oligonucleotide of the present invention having a WC domain that is complementary to the target mRNA.

The present invention also contemplates labeling the subject oligonucleotides for use as probes to detect a target nucleic acid. Labelled circular oligonucleotide probes have utility in diagnostic and analytical hybridization procedures for localizing, quantitating or detecting a target nucleic acid in tissues, chromosomes or in mixtures of nucleic acids. Labeling of a stem-loop or circular oligonucleotide can be accomplished by incorporating nucleotides linked to a reporter group into the subject oligonucleotides. A reporter group, as defined herein, is a molecule or group which, by its chemical nature, provides an identifiable signal allowing detection of the circular oligonucleotide. Detection can be either qualitative or quantitative. The present invention contemplates using any commonly used reporter molecule including radionuclides, enzymes, biotins, psoralens, fluorophores, chelated heavy metals, and luciferin. The most commonly used reporter molecules are either enzymes, fluorophores or radionuclides linked to the nucleotides which are used in circular oligonucleotide synthesis. Commonly used enzymes include horseradish peroxidase, alkaline phosphatase, glucose oxidase and β-galactosidase, among others. The substrates to be used with the specific enzymes are generally chosen because a detectably colored product is formed by the enzyme acting upon the substrate. For example, p-nitrophenyl phosphate is suitable for use with alkaline phosphatase conjugates; for horseradish peroxidase, 1,2-phenylenediamine, 5-aminosalicyclic acid or toluidine are commonly used. Fluorophores may be detected for example by microscopy or digital imaging. Similarly, methods for detecting radionucleotides are well-known in the art. The probes so generated have utility in the detection of a specific DNA or RNA target in, for example, Southern analysis, Northern analysis, in situ hybridization to tissue sections or chromosomal squashes and other analytical and diagnostic procedures. The methods of using such hybridization probes are well known and examples of such methodology are provided by Sambrook et al.

The present stem-loop and circular oligonucleotides can be used in conjunction with any known detection or diagnostic procedure which is based upon hybridization of a probe to a target nucleic acid. Moreover, the present oligonucleotides can be used in any hybridization procedure which quantitates a target nucleic acid, e.g., by competitive hybridization between a target nucleic acid present in a sample and a labeled tracer target for one of the present oligonucleotides. Furthermore, the reagents needed for making a stem-loop or circular oligonucleotide probe and for utilizing such a probe in a hybridization procedure can be provided in a kit.

The kit can be compartmentalized for ease of utility and can contain at least one first container providing reagents for making a precircle precursor for a circular oligonucleotide, at least one second container providing reagents for labeling the precircle with a reporter molecule, at least one third container providing regents for circularizing the precircle, and at least one fourth container providing reagents for isolating the labeled circular oligonucleotide.

Moreover the present invention provides a kit for isolation of a template nucleic acid. Such a kit has at least one first container providing a stem-loop or circular oligonucleotide having a WC domain that is complementary to a target contained within the template.

Further, a kit for the detection of any target nucleic acid is provided which contains an oligonucleotide of the present invention linked to a reporter group. Additional containers providing reagents for detecting a linked reporter group can also be provided in the kit.

Furthermore, the present invention provides kits useful when diagnosis of a disease depends upon detection of a specific, known target nucleic acid. Such nucleic acid targets can be, for example, a viral nucleic acid, an extra or missing chromosome or gene, a mutant cellular gene or chromosome, an aberrantly expressed RNA and others. The kits can be compartmentalized to contain at least one first container providing a stem-loop or circular oligonucleotide linked to a reporter molecule and at least one second container providing reagents for detection of the reporter molecule.

Therefore, as contemplated by the present invention, the kits disclosed herein can include any elements recognized or conventionally used by the skilled artisan for constructing, purifying and using oligonucleotides. Moreover, the present kits can include specific chemical reagents or end-joining-oligonucleotides for making the present circular oligonucleotides.

One aspect of the present invention provides a method of regulating biosynthesis of a DNA, an RNA or a protein by contacting at least one of the subject stem-loop or circular oligonucleotides with a nucleic acid template for that DNA, that RNA or that protein in an amount and under conditions sufficient to permit the binding of the oligonucleotide to a target sequence contained in the template. The binding between the oligonucleotide and the target blocks access to the template, and thereby regulates biosynthesis of the nucleic acid or the protein. Blocking access to the template prevents proteins and nucleic acids involved in the biosynthetic process from binding to the template, from moving along the template, or from recognizing signals encoded within the template. Alternatively, when the template is RNA, regulation can be accomplished by allowing selective degradation of the template. For example, RNA templates bound by the subject oligonucleotides are susceptible to degradation by RNase H and RNase H. Degradation of a selected RNA template can thereby regulate use of the template in biosynthetic processes.

As used herein, biosynthesis of a nucleic acid or a protein includes cellular and viral processes such as DNA replication, DNA reverse transcription, RNA transcription, RNA splicing, RNA polyadenylation, RNA translocation and protein translation, all of which can lead to production of DNA, RNA or protein, and involve a nucleic acid template at some stage of the biosynthetic process.

As used herein, regulating biosynthesis includes inhibiting, stopping, increasing, accelerating or delaying biosynthesis. Regulation may be direct or indirect, i.e. biosynthesis of a DNA, RNA or protein may be regulated directly by binding a stem-loop or circular oligonucleotide to the template for that DNA, RNA or protein; alternatively, biosynthesis may be regulated indirectly by oligonucleotide binding to a second template encoding a protein that plays a role in regulating the biosynthesis of the first DNA, RNA or protein. In a preferred embodiment, the subject oligonucleotides are used to arrest translation, reverse transcription, or replication.

DNA replication from a DNA template is mediated by proteins which bind to an origin of replication where they open the DNA and initiate DNA synthesis along the DNA template. To inhibit DNA replication in accordance with the present invention, oligonucleotides are selected which bind to one or more targets in an origin of replication. Such binding blocks template access to proteins involved in DNA replication. Therefore initiation and procession of DNA replication is inhibited. As an alternative method of inhibiting DNA replication, expression of the proteins which mediate DNA replication can be inhibited at, for example, the transcriptional or translational level. As one skilled in the art recognizes, DNA replication can also be increased, e.g. by inhibiting expression of a protein repressor of DNA replication.

DNA replication from an RNA template is mediated by reverse transcriptase binding to a region of RNA also bound by a nucleic acid primer. To inhibit DNA replication from an RNA template, reverse transcriptase or primer binding can be blocked by binding a stem-loop or circular oligonucleotide to the primer binding site, and thereby blocking access to that site. Moreover, inhibition of DNA replication can occur by binding a stem-loop or circular oligonucleotide to a site residing in the RNA template since such binding can block access to that site and to downstream sites, i.e. sites on the 3' side of the target site.

To initiate RNA transcription, RNA polymerase recognizes and binds to specific start sequences, or promoters, on a DNA template. Binding of RNA polymerase opens the DNA template. There are also additional transcriptional regulatory elements that play a role in transcription and are located on the DNA template. These transcriptional regulatory elements include enhancer sequences, upstream activating sequences, repressor binding sites and others. All such promoter and transcriptional regulatory elements, singly or in combination, are targets for the subject circular oligonucleotides. Oligonucleotide binding to these sites can block RNA polymerase and transcription factors from gaining access to the template and thereby regulating, e.g., increasing or decreasing, the production of RNA, especially mRNA and tRNA. Additionally, the subject oligonucleotides can be targeted to the coding region or 3'-untranslated region of the DNA template to cause premature termination of transcription. One skilled in the art can readily design oligonucleotides for the above target sequences from the known sequence of these regulatory elements, from coding region sequences, and from consensus sequences.

Protein biosynthesis begins with the binding of ribosomes to an mRNA template, followed by initiation and elongation of the amino acid chain via translational "reading" of the mRNA. Protein biosynthesis, or translation, can thus be blocked or inhibited by blocking access to the template using the subject oligonucleotides to bind to targets in the template mRNA. Such targets contemplated by this invention include the ribosome binding site (Shine-Delgarno sequence), the 5' mRNA cap site, the initiation codon, and sites in the protein coding sequence. There are also classes of protein which share domains of nucleotide sequence homology. Thus, inhibition of protein biosynthesis for such a class can be accomplished by targeting the homologous protein domains (via the coding sequence) with the subject circular oligonucleotides.

Regulation of biosynthesis by any of the aforementioned procedures has utility for many applications. For example, genetic disorders can be corrected by inhibiting the production of mutant or over-produced proteins, or by increasing production of under-expressed proteins; the expression of genes encoding factors that regulate cell proliferation can be inhibited to control the spread of cancer; and virally encoded functions can be inhibited to combat viral infection.

In accordance with the present invention, it has been determined that in some instances the biosynthesis of a DNA, RNA or protein is more effectively regulated by binding the template at more than one target site. The present stem-loop and circular oligonucleotides which are prepared to bind to multiple target sites, e.g. by having more than one WC and H domain, can also be more effective at regulating the biosynthesis of a DNA, RNA or protein than oligonucleotides that can bind only one target site. For example, the binding of two sites within a gene can provide greater inhibition than achieved with single-site binding (Lisziewicz et al., 1992, *Proc. Natl. Acad. Sci. USA* 89:11209; Maher et al., 1987, *J. Arch. Biochem. Biophys.* 253:214–220; Tannock, I. F. in "The Basic Science of Oncology" 2nd ed.; Tannock, I. F. and Hill, R. P., eds. McGraw-Hill, New York, 348–349). In targeting viral sequences, the binding of two genes in a virus can inhibit viral replication more effectively than binding a single target. It has been shown, for example, that the use of multiple probes against a virus reduces the ability of the virus to escape inhibition by mutation (Kern et al., 1991, *Science* 252:1708–1711). A broader spectrum of inhibition by targeting two mutants of one virus or two viruses which are commonly found together, such as HIV-1 and cytomegalovirus (CMV) can also be achieved in accordance with the present invention.

Therefore, the present methods of regulating the biosynthesis of a DNA, RNA or protein can also include binding to more than one target within a template, whether the targets are bound by separate stem-loop and circular oligonucleotides or by the same oligonucleotide which includes multiple WC and H domains.

Some types of genetic disorders that can be treated by the circular oligonucleotides of the present invention include Alzheimer's disease, beta-thalassemia, some types of arthritis, sickle cell anemia, osteogenesis imperfecta and others. Many types of viral infections can be treated by utilizing the oligonucleotides of the present invention, including infections caused by influenza, hepatitis, rhinovirus, HIV, herpes simplex, papilloma virus, cytomegalovirus, Epstein-Barr virus, adenovirus, vesticular stomatitus virus, rotavirus and respiratory syncytial virus among others. According to the present invention, animal and plant viral infections may also be treated by administering the subject oligonucleotides.

Human immunodeficiency virus (HIV) is a retrovirus causing acquired immunodeficiency syndrome (AIDS). The stem-loop and circular oligonucleotides of this invention provide a means of blocking the replication of the virus without deleteriously affecting normal cellular replication in humans infected with HIV. Inhibition of HIV infection can be accomplished by designing oligonucleotides to bind to a number of regions within the HIV genome, including coding regions for functions that replicate the genome (i.e., the pol or reverse transcriptase function) or functions that control gene expression (e.g. the tat, rev or other functions). Previous work with linear oligonucleotides has suggested that splice sites, poly(A) addition signals, cap or initiator codon sites, and sites implicated in ribosome assembly can be particularly effective for inhibiting eucaryotic protein expression. Furthermore, the terminal structures of the retroviral genome are also excellent targets for inhibiting retrovirus production not only because these structures encode control regions which mediate the rate of transcription and replication, but also because these structures are repeated, allowing an oligonucleotide to bind and block access to each repeat.

In vitro screening for stem-loop or circular oligonucleotide effectiveness against HIV infection permits one skilled in the art to judge the stability of oligonucleotide: target binding and to assess in vivo efficacy and binding stability. To observe in vitro inhibition, stem-loop or circular oligonucleotides can be added to the growth medium of an appropriate cell line infected with HIV. Cells can be pre-treated with the subject oligonucleotides or the oligonucleotides can be added at the time of infection or after HIV infection. Addition before or after infection allows assessment of whether the subject oligonucleotide can prevent or simply inhibit HIV infection respectively.

The extent of inhibition of HIV infection or replication can be judged by any of several assay systems, including assessment of the proportion of oligonucleotide-treated cells surviving after infection relative to survival of untreated cells, assessment of the number of syncytia formed in treated and untreated HIV infected cells and determination of the amount of viral antigen produced in treated and untreated cells.

In vivo studies of the efficacy of subject oligonucleotides can be done in a suitable animal host, such as transgenic mice, immune deficient mice or chimpanzees. Levels of HIV antigens can be monitored to assess the effect of subject oligonucleotides on HIV replication and thereby to follow the course of the disease state. Alternatively, human volunteers with AIDS or ARC can be administered with the subject circular oligonucleotides since the oligonucleotides do not appear to be cytotoxic. The disease status of these volunteers can then be assessed to determine the efficacy of the subject oligonucleotides in treating and preventing AIDS infection.

A further aspect of this invention provides pharmaceutical compositions containing the subject stem-loop or circular oligonucleotides with a pharmaceutically acceptable carrier. In particular, the subject oligonucleotides are provided in a therapeutically effective amount of about 0.1 µg to about 100 mg per kg of body weight per day, and preferably of about 0.1 µg to about 10 mg per kg of body weight per day, to bind to a nucleic acid in accordance with the methods of this invention. Dosages can be readily determined by one of ordinary skill in the art and formulated into the subject pharmaceutical compositions.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The subject oligonucleotides may be administered topically or parenterally by, for example, by osmotic pump, intravenous, intramuscular, intraperitoneal subcutaneous or intradermal route, or when suitably protected, the subject oligonucleotides may be orally administered. The subject oligonucleotides may be incorporated into a cream, solution or suspension for topical administration. For oral administration, oligonucleotides may be protected by enclosure in a gelatin capsule. Oligonucleotides may be incorporated into liposomes or liposomes modified with polyethylene glycol or admixed with cationic lipids for parenteral administration. Incorporation of additional substances into the liposome, for example, antibodies reactive against membrane proteins found on specific target cells, can help target the oligonucleotides to specific cell types. Stem-loop oligonucleotides may be delivered as an expression vector.

Moreover, the present invention contemplates administering the subject oligonucleotides with an osmotic pump providing continuous infusion of such oligonucleotides, for example, as described in Rataiczak et al. (1992, Proc. Natl. Acad. Sci. USA 89:11823–11827). Such osmotic pumps are commercially available, e.g., from Alzet Inc (Palo Alto, Calif.). Topical administration and parenteral administration in a cationic lipid carrier are preferred modes of administration.

The following examples further illustrate the invention.

EXAMPLE 1

Design and Synthesis of Oligonucleotides

Four deoxynucleotides were designed to bind the 12-mer target sequences 5'-dCTCCTCCCTCCT (SEQ ID NO:1) and 5'-rCUCCUCCCUCCU (SEQ ID NO:2) by conventional Watson-Crick base pairing or by the formation of pur•pur•pyr triplexes. The oligonucleotides are as follows:

Oligonucleotide 1: 5'-AGGAGGGAGGAG (SEQ ID NO:3)
Oligonucleotide 2: 5'-AGGAGGGAGGAGCACACGTGGTGGGTGGT (SEQ ID NO:4)

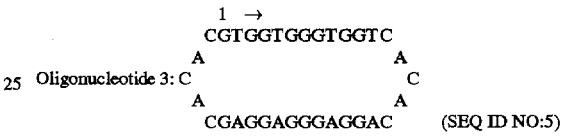

Oligonucleotide 4:
5'-AGGAGGGAGGAGCACACGTGGTGTGTGGT (SEQ ID NO:6)

Oligonucleotide 1 is the Watson-Crick complement of the target sequence. Linear oligonucleotide 2 and circular oligonucleotide 3 each contain a 12-nucleotide domain that is complementary to the target in antiparallel Watson-Crick sense, and an opposing 12-nucleotide domain that is complementary to the first domain in antiparallel reverse Hoogsteen sense. Oligonucleotide 4 is similar to oligodeoxynucleotide 2 but contains a single mismatch in the Hoogsteen domain.

The strategy for binding of oligonucleotides 1–4 to the target strand is illustrated in Table 1 wherein short lines denote Watson-Crick hydrogen bonds and dots indicate Hoogsteen bonds.

DNA oligomers were synthesized on an Applied Biosystems 392 automated synthesizer using the standard phosphoramidite method described by Beaucage et al. (1981) Tetrahedron Lett. 22:1859. RNA oligonucleotides were prepared using t-butyl-dimethylsilyl-protected phosphoramidites (Applied Biosystems), and following the oligoribonucleotide synthesis procedure of Scaringe et al. (1990) Nucleic Acids Res. 18:5433. Tetrabutylammonium fluoride in THF (Aldrich) was dried over molecular sieves prior to use in the desilylation step as described by Horn et al. (1986) Tetrahedron Lett. 27:4705. For synthesis of circular DNAs the linear precursors were 5'-phosphorylated on the synthesizer using a commercially available reagent purchased from Cruachem as described by Hogrefe et al. (1993) Nucleic Acids Res. 21:4739. Oligonucleotides were purified by preparative 20% denaturing polyacrylamide gel electrophoresis and quantitated by absorbance at 260 nm. Extinction coefficients for the oligomers were calculated by the nearest neighbor method of Borer (1985) in G. D. Fasman (ed.) Handbook of Biochemistry and Molecular Biology, 3rd Ed. CRC Press, Cleveland, Vol. I, p. 589.

The cyclizations of the 5'-phosphorylated precursor of circular ligand 3 was carried out essentially as described by Prakash et al. (1992) J. Am. Chem. Soc. 114:3523 and Wang et al. (1994) *Nucleic Acids Res.* 22:2326. The precursor was reacted at 50 μM concentration; the cyclization of 3 was aided by the template dCTCCTCCCTCCT (SEQ ID NO:1) (55 μM). The ligation was carried out in a buffer containing imidazole-HCl (200 mM, from a 0.5M pH 7.0 stock), and $NiCl_2$ (100 mM). Solid BrCN was added with vortex mixing to give a final calculated concentration of 125 mM, and the reaction was allowed to proceed at 25° C. for 12 hr. As the reaction proceeded a light tan precipitate was observed, and previous studies have shown that this precipitate contains the majority of the nucleic acids. The solution (including solids) was dialyzed against water and lyophilized. The resulting solid was loaded onto a preparative 20% denaturing polyacrylamide gel for separation. The circular product was isolated by excision from the gel after visualization by UV shadowing; the circle 3 migrated at a rate ~0.9 times that of the linear 34-mer precursor.

The circularity of 3 was confirmed by partial digestion by S1 nuclease. The reaction was carried out using 1 nmol DNA in 5.1 μL of a buffer containing 50 mM NaOAc, 50 mM NaCl, and 5 mM $ZnCl_2$. Then 0.4 units nuclease S1 (0.9 μL, Pharmacia) was added, and the mixture incubated at 37° C. for 10 min. The reaction was stopped by addition of 6 μL of an 8M urea, 30 mM EDTA solution, and the mixture was loaded onto a 20% denaturing analytical polyacrylamide gel. Products were visualized for photography with Stains-all dye (Sigma). The compound showed a single initial product which migrates with the mobility of the 34-mer precursor.

EXAMPLE 2

Binding Properties of Linear and Circular Oligonucleotides

The binding properties of oligonucleotides 1–4 were characterized by thermal denaturation and gel titration studies with DNA and RNA target strands monitored at 260 nm.

Solutions for the thermal denaturation studies contained a 1:1 molar ratio of oligonucleotide ligand and complementary 12-nt pyrimidine target (1 μM each). Solutions were buffered with 10 mM Na•PIPES (1,4-piperazine-bis (ethanesulfonate), Sigma) at pH 7.0 or at pH 5.5. The buffer pH is that of a 500 mM stock solution at 25° C.; after dilution the final solution pH was shown to be within 0.1 unit of the buffer stock. Also present in the denaturation solutions were 100 mM NaCl and 10 mM $MgCl_2$. After preparation the solutions were heated to 90° C. and allowed to cool slowly to room temperature prior to the melting experiments.

The melting studies were carried out in teflon-stoppered 1 cm pathlength quartz cells under nitrogen atmosphere on a Varian Cary 1 UV-vis spectrophotometer equipped with thermoprogrammer. Absorbance (260 nm) was monitored while temperature was raised from 5.0 to 95° C. at a rate of 0.5° C./min. Melting temperatures ($T_m$) were determined by computer fit of the first derivative of absorbance with respect to 1/T. Uncertainty in $T_m$ is estimated at ±0.5° C. based on repetitions of experiments.

Free energies were determined by curve fitting as described by Petersheim et al. (1982) *Biochemistry* 22:256. Values at 60° C. are more accurate than those at 37° C. because of smaller extrapolation from the $T_m$ values.

For gel titration studies; pH 7.0 solutions of ratio 2:1, 1:1 and 1:2 circle:substrate oligomer (0.25 or 0.5 nmol each) were prepared at 4° C. in 5 μL of a buffer containing 70 mM Tris•borate, 10 mM $MgCl_2$, and 6% glycerol and incubated for 4 hr prior to loading on a 20% nondenaturing PAGE gel. The gels were electrophoresed at 2.5 mW at 4° C. using the same buffer as the electrophoresis buffer, and the resulting bands were visualized with Stains-all dye.

Results of binding studies of oligomers 1–4 with complementary single stranded DNA targets are shown in Table 1.

TABLE 1

Melting Transition Temperatures ($T_m$ (°C.)) and Free Energies (−ΔG° (kcal/mol)) for Complexes of Linear and Circular Purine-Rich DNAs with Complementary Pyrimidine DNA Single Strands at pH 7.0 (Lines Indicate Watson-Crick Complementarity, Dots Hoogsteen Complementarity, and Arrows 5' to 3' Directionality[a])

| OLIGONU-CLEOTIDE | COMPLEX | $T_m$(°C.)[a] | $-\Delta G°_{37}$[a] (kcal/mol) | $-\Delta G°_{60}$[a] (kcal/mol) |
|---|---|---|---|---|
| 1 | 3'-GAGGAGGGAGGA<br>\|\|\|\|\|\|\|\|\|\|\|\|<br>5'-CTCCTCCCTCCT | 56.9 | 14.2 | 8.4 |
| 2 | C GTGGTGGGTGGT<br>A<br>C ............<br>A<br>C GAGGAGGGAGGA-5'<br>\|\|\|\|\|\|\|\|\|\|\|\|<br>5'-CTCCTCCCTCCT | 68.4 | 16.9 | 11.6 |
| 3 | →<br>C GTGGTGGGTGGT  C<br>A                            A<br>C ............      C<br>A                            A<br>C . GAGGAGGGAGGA C<br>\|\|\|\|\|\|\|\|\|\|\|\|<br>5'-CTCCTCCCTCCT | 71.0 | 17.3 | 12.0 |

TABLE 1-continued

Melting Transition Temperatures ($T_m$ (°C.)) and Free Energies
($-\Delta G°$ (kcal/mol)) for Complexes of Linear and Circular Purine-Rich DNAs
with Complementary Pyrimidine DNA Single Strands at pH 7.0 (Lines
Indicate Watson-Crick Complementarity, Dots Hoogsteen Complementarity,
and Arrows 5' to 3' Directionality[a])

| OLIGONU-CLEOTIDE | COMPLEX | $T_m$(°C.)[a] | $-\Delta G°_{37}$[a] (kcal/mol) | $-\Delta G°_{60}$[a] (kcal/mol) |
|---|---|---|---|---|
| 4 | C GTGGTGTGTGGT<br>A<br>C       X<br>A<br>C GAGGAGGGAGGA-5'<br>\|\|\|\|\|\|\|\|\|\|\|\|<br>5'-CTCCTCCCTCCT | 61.9 | 12.4 | 9.4 |

[a]Uncertainties in $T_m$ values and in free energies are estimated at ±1.0° C. and ±15%, respectively.

The results in Table I show that oligonucleotides 2 and 3 do in fact bind the 12-mer DNA target, and with considerably higher affinity than does the Watson-Crick 12-mer complement (oligonucleotide 1).

Specifically, oligonucleotide 2 binds dCTCCTCCCTCCT (SEQ. ID. NO:1) with a $T_m$ of 68.4° C. (conditions: pH 7.0 (10 mM Na-PIPES buffer), 100 mM Na$^+$, 10 mM Mg$^{2+}$) and a free energy estimated at $-16.9$ kcal/mol at 37° C. This is in contrast to the simple 12-mer Watson-Crick complement oligonucleotide 1, which binds with a $T_m$ of 56.9° C. and a free energy of $-14.2$ kcal/mol under identical conditions. The closed circular oligonucleotide 3 binds the target with the highest thermal stability, with a $T_m$ of 71.0° C. and a free energy of $-17.3$ kcal/mol. This represents an advantage of 2 orders of magnitude in association constant over simple Watson-Crick recognition. A similar advantage is seen in free energies calculated at 60° C.

The stoichiometry of the complex of 3 was measured by titration of the target with the ligand, monitored by denaturing gel electrophoresis. This confirmed 1:1 stoichiometry as predicted for the expected triple-helical complex. The single-mismatched oligonucleotide 4 was also hybridized to the pyrimidine complement. Results show that it binds the DNA target with significantly lower affinity; this confirms the importance of the Hoogsteen strand in increasing the affinity of binding, even though it presumably does not come in direct contact with the target.

The binding of oligonucleotide 3 to the single stranded DNA target was not significantly pH dependent, giving the same $T_m$, within experimental error, at pH 5.5. as that measured at pH 7.0.

Results of binding studies of oligonucleotides 1-4 with complementary single stranded RNA targets are shown in Table 2.

TABLE 2

Melting Transition Temperatures ($T_m$ (°C.)) and Free Energies
($-\Delta G°$ (kcal/mol)) for Complexes of Linear and Circular Purine-Rich DNAs
with Complementary Pyrimidine RNA Single Strands at pH 7.0 (Lines
Indicate Watson-Crick Complementarity, Dots Hoogsteen Complementarity,
and Arrows 5' to 3' Directionality[a]

| OLIGONU-CLEOTIDE | COMPLEX | $T_m$(°C.)[a] | $-\Delta G°_{37}$[a] (kcal/mol) | $-\Delta G°_{60}$[a] (kcal/mol) |
|---|---|---|---|---|
| 1 | 3'-dGAGGAGGGAGGG<br>\|\|\|\|\|\|\|\|\|\|\|\|<br>5'-rCUCCUCCCUCCU | 58.9 | 15.6 | 8.3 |
| 2 | C GTGGTGGGTGGT<br>A<br>C   . . . . . . . . . . .<br>A<br>C GAGGAGGGAGGA-5'<br>\|\|\|\|\|\|\|\|\|\|\|\|<br>5'-rCUCCUCCCUCCU | 65.3 | 14.5 | 10.4 |
| 3 | →<br>C GTGGTGGGTGGT   C<br>A                       A<br>C   . . . . . . . . . . .   C<br>A                       A<br>C . GAGGAGGGAGGA C<br>\|\|\|\|\|\|\|\|\|\|\|\|<br>5'-rCUCCUCCCUCCU | 69.2 | 15.4 | 11.2 |

TABLE 2-continued

Melting Transition Temperatures ($T_m$ (°C.)) and Free Energies (−ΔG° (kcal/mol)) for Complexes of Linear and Circular Purine-Rich DNAs with Complementary Pyrimidine RNA Single Strands at pH 7.0 (Lines Indicate Watson-Crick Complementarity, Dots Hoogsteen Complementarity, and Arrows 5' to 3' Directionality[a]

| OLIGONU-CLEOTIDE | COMPLEX | $T_m$(°C.)[a] | −ΔG°$_{37}$[a] (kcal/mol) | −ΔG°$_{60}$[a] (kcal/mol) |
|---|---|---|---|---|
| 4 | C GTGGTGTGTGGT<br>A<br>C      X<br>A<br>C GAGGAGGGAGGA-5'<br>||||||||||||<br>5'-rCUCCUCCCUCCU | 64.3 | 15.3 | 10.3 |

[a]Uncertainties in $T_m$ values and in free energies are estimated at ±1.0° C. and ±15%, respectively.

As shown in Table 2, oligonucleotides 2 and 3 also bind single-stranded RNA with high affinity. Hairpin-shaped oligonucleotide 2 binds rCUCCUCCCUCCU with a $T_m$ of 65.3° C., for an advantage of 5.4° C. over the Watson-Crick complement, and circular oligonucleotide 3 binds with the highest thermal stability, with a $T_m$ advantage of 10.3° C. over simple Watson-Crick binding. The estimated free energies at 37° C. do not reflect this difference; however, more accurate values calculated for 60° C. do mirror the advantage seen in the melting temperatures. Mismatched oligonucleotide 4 binds the RNA target somewhat less strongly than the fully complementary hairpin. There is a clear binding advantage for circular ligands over the simple Watson-Crick complement. The data in Tables 1 and 2 demonstrate that both DNA and RNA strands can be strongly bound using the same DNA ligands.

EXAMPLE 3

Circular DNA Oligonucleotides Bind with High Affinity to DNA and RNA Targets

A circular DNA (oligonucleotide 5) having the sequence:

```
        1→
        GTGGTGGGTGGT
      C            C
      C            C
        GAGGAGGGAGGA        (SEQ ID NO:7)
``` was synthesized by the method described in Example 1.
The following targets were also synthesized:

5'-rCUCCUCCCUCCU (SEQ ID NO:2)

| | |
|---|---|
| 5'-dCTCCTCCCTCCT | (SEQ ID NO:1) |
| 5'-dCCCCCACTCCTCCCTCCTACCCCC | (SEQ ID NO:8) |

SEQ ID NO:8 represents a "long" target in which the sequence complementary to the WC domain is embedded in a longer template.

Binding properties of oligonucleotide 8 to the RNA target (SEQ ID NO:2), short DNA target (SEQ ID NO:1) and long DNA target (SEQ ID NO:8) were assessed by the method described in Example 2. The results in Table 3 demonstrate that the circular DNA binds with high affinity to DNA and RNA targets.

TABLE 3

Melting transition temperature ($T_m$(°C.)) and Free Engergies (−ΔG°$_{37}$ (kcal/mol)) for complexes of Oligonucleotide 5 with Complementary Pyrimidine DNA and RNA single Strands at pH 7.0

| TARGET | $T_m$(°C.)[a] | −ΔG°$_{37}$[a] (kcal/mol) |
|---|---|---|
| RNA (SEQ ID NO:2) | 71.7 | 12.5 |
| short DNA (SEQ ID NO:1) | 70.5 | 12.3 |
| long DNA (SEQ ID NO:8) | 69.6 | 11.9 |

[a]Error in $T_m$ values and in free energies are estimated at ±1.0° C. and ±15%, respectively.

What is claimed is:

1. A circular oligonucleotide comprising at least one first binding domain capable of detectably binding to a nucleic acid target by antiparallel Watson-Crick base pairing and at least one second binding domain capable of binding to said first binding domain by antiparallel Hoogsteen base pairing.

2. A stem-loop oligonucleotide comprising a double-stranded stem domain of at least two base pairs and a loop domain comprising at least one first binding domain capable of detectably binding to a nucleic acid target by antiparallel Watson-Crick base pairing and at least one second binding domain capable of binding to said first binding domain by antiparallel Hoogsteen base pairing.

3. The oligonucleotide of claim 1 or 2 further comprising a linker domain separating each of said binding domains.

4. The oligonucleotide of claim 1 or 2 wherein said target is DNA or RNA.

5. The oligonucleotide of claim 4 wherein said DNA or said RNA is single-stranded.

6. The oligonucleotide of claim 1 or 2 wherein said nucleic acid target is pyrimidine rich.

7. The oligonucleotide of claim 1 or 2 wherein said first binding domain is from about 50% to about 100% complementary to said target.

8. The oligonucleotide of claim 7 wherein said first binding domain is from about 90% to about 100% complementary to said target.

9. The oligonucleotide of claim 1 or 2 wherein said target is U and C or T and C rich, said first domain is A and G rich and said second domain is T and G or A and G rich.

10. The oligonucleotide of claim 1 or claim 2, wherein said oligonucleotide consists of ribonucleotides, deoxyribonucleotides, or both ribonucleotides and deoxyribonucleotides.

11. The oligonucleotide of claim 1 or 2 wherein said binding domains are RNA and said nucleic acid target is RNA.

12. The oligonucleotide of claim 1 or 2 wherein said binding domains are DNA and said nucleic acid target is RNA.

13. The oligonucleotide of claim 1 or 2 wherein said binding domains are DNA and said nucleic acid target is DNA.

14. The oligonucleotide of claim 3 wherein said linker domain consists of 1 to 10 nucleotides.

15. The oligonucleotide of claim 3 wherein said linker domain consists of 2 or 3 nucleotides.

16. The oligonucleotide of claim 3 wherein said linker domain is a non-nucleotide linker domain.

17. The oligonucleotide of claim 16 wherein said non-nucleotide linker domain is polyethylene glycol.

18. The oligonucleotide of claim 1 or 2 wherein said first and said second binding domains independently are from 2 to about 200 nucleotides.

19. The oligonucleotide of claim 18 wherein said first and said second binding domains independently are from 8 to 36 nucleotides.

20. A complex of the oligonucleotide of claim 1 or 2 and a nucleic acid target.

21. A kit for detection, diagnosis or isolation of a target nucleic acid comprising at least one first container providing the oligonucleotide of claim 1 or 2.

22. The oligonucleotide of claim 1 or 2 further comprising a reporter group.

23. A kit for the detection, diagnosis or isolation of a target nucleic acid comprising at least one first container providing the oligonucleotide of claim 22.

24. A method of detecting a target nucleic acid which comprises:

contacting a sample to be tested for containing said target nucleic acid with an oligonucleotide of claim 1 or 2 for a time and under conditions sufficient to form an oligonucleotide-target complex; and detecting said complex.

25. The method of claim 24 wherein said target nucleic acid is selected from the group consisting of single-stranded nucleic acids or double stranded nucleic acids.

26. The method of claim 24 wherein said sample is selected from the group consisting of pure nucleic acid samples, impure nucleic acid samples, tissue sections, cell smears or chromosomal squashes.

27. A circular oligonucleotide comprising a first binding domain capable of binding in an antiparallel manner to a nucleic acid target and a second binding domain capable of binding in an antiparallel manner to said first binding domain wherein the sequences of said binding domains are determined with reference to said nucleic acid target such that:

when a base for a position in said target is adenine or an adenine analog, the corresponding base in said first domain is thymine or uracil or suitable analogs thereof and the corresponding base in said second domain is adenine, cytosine, guanine, thymine, uracil, imidazole or suitable analogs thereof;

when a base for a position in said target is guanine or a guanine analog, the corresponding base in said first domain is cytosine or uracil or suitable analogs thereof and the corresponding base in said second domain is adenine, cytosine, guanine, thymine, uracil, imidazole or suitable analogs thereof;

when a base for a position in said target is cytosine or a cytosine analog, the corresponding base in said first domain is guanine or a suitable analog thereof and the corresponding base in said second domain is guanine or a suitable analog thereof;

when a base for a position in said target is thymine or a thymine analog, the corresponding base in said first domain is adenine or a suitable analog thereof and the corresponding base in said second domain is adenine or thymine or uracil or suitable analogs thereof; and when a base for a position in said target is uracil or an analog thereof, the corresponding base in said first domain is adenine or a suitable analog thereof and the corresponding base in said second domain is adenine or thymine or uracil or suitable analogs thereof.

28. A stem-loop oligonucleotide comprising a first binding domain capable of binding in an antiparallel manner to a nucleic acid target and a second binding domain capable of binding in an antiparallel manner to said first binding domain wherein the sequences of said binding domains are determined with reference to said nucleic acid target such that:

when a base for a position in said target is adenine or an adenine analog, the corresponding base in said first domain is thymine or uracil or suitable analogs thereof and the corresponding base in said second domain is adenine, cytosine, guanine, thymine, uracil, imidazole or suitable analogs thereof;

when a base for a position in said target is guanine or a guanine analog, the corresponding base in said first domain is cytosine or uracil or suitable analogs thereof and the corresponding base in said second domain is adenine, cytosine, guanine, thymine, uracil, imidazole or suitable analogs thereof;

when a base for a position in said target is cytosine or a cytosine analog, the corresponding base in said first domain is guanine or a suitable analog thereof and the corresponding base in said second domain is guanine or a suitable analog thereof;

when a base for a position in said target is thymine or a thymine analog, the corresponding base in said first domain is adenine or a suitable analog thereof and the corresponding base in said second domain is adenine or thymine or uracil or suitable analogs thereof; and when a base for a position in said target is uracil or an analog thereof, the corresponding base in said first domain is adenine or a suitable analog thereof and the corresponding base in said second domain is adenine or thymine or uracil or suitable analogs thereof.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 12 base pairs
        ( B ) TYPE: nucleic acid
        ( C ) STRANDEDNESS: single ( D ) TOPOLOGY: linear ( x i ) SEQUENCE DESCRIPTION: SEQ ID NO:1:

CTCCTCCCTC CT    12

( 2 ) INFORMATION FOR SEQ ID NO:2:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CUCCUCCCUC CU    12

( 2 ) INFORMATION FOR SEQ ID NO:3:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

AGGAGGGAGG AG    12

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

AGGAGGGAGG AGCACACGTG GTGGGTGGT    29

( 2 ) INFORMATION FOR SEQ ID NO:5:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: circular ( x i ) SEQUENCE DESCRIPTION: SEQ ID NO:5:

GTGGTGGGTG GTCACACAGG AGGGAGGAGC ACAC    34

( 2 ) INFORMATION FOR SEQ ID NO:6:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

AGGAGGGAGG AGCACACGTG GTGTGTGGT    29

( 2 ) INFORMATION FOR SEQ ID NO:7:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: circular ( x i ) SEQUENCE DESCRIPTION: SEQ ID NO:7:

GTGGTGGGTG GTCCAGGAGG GAGGAGCC         28

( 2 ) INFORMATION FOR SEQ ID NO:8:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:8:

CCCCCACTCC TCCCTCCTAC CCCC         24